US012558078B2

(12) United States Patent
Fujii et al.

(10) Patent No.: US 12,558,078 B2
(45) Date of Patent: Feb. 24, 2026

(54) ENDOSCOPIC VESSEL HARVESTER WITH GYROSENSOR ON HANDLE FOR ROTATING CAMERA VIEW

(71) Applicant: TERUMO CARDIOVASCULAR SYSTEMS CORPORATION, Ann Arbor, MI (US)

(72) Inventors: Tatsunori Fujii, Bear, DE (US); Randal J. Kadykowski, South Lyon, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 628 days.

(21) Appl. No.: 17/498,891

(22) Filed: Oct. 12, 2021

(65) Prior Publication Data

US 2022/0022948 A1 Jan. 27, 2022

Related U.S. Application Data

(63) Continuation of application No. PCT/US2020/029498, filed on Apr. 23, 2020.
(Continued)

(51) Int. Cl.
*A61B 1/05* (2006.01)
*A61B 1/00* (2006.01)
(Continued)

(52) U.S. Cl.
CPC .. *A61B 17/00008* (2013.01); *A61B 1/000094* (2022.02); *A61B 1/00097* (2022.02);
(Continued)

(58) Field of Classification Search
CPC ........ A61B 17/00008; A61B 1/000094; A61B 1/00097; A61B 18/1482; A61B 90/37;
(Continued)

(56) References Cited

U.S. PATENT DOCUMENTS 6,471,637 B1 10/2002 Green et al.
7,037,258 B2 5/2006 Chatenever et al.
(Continued)

FOREIGN PATENT DOCUMENTS

JP H10-020214 1/1998
JP 2005-246058 9/2005
(Continued)

OTHER PUBLICATIONS

Japanese Official Action, Application No. 2021-564489, dated Oct. 17, 2023.
(Continued)

*Primary Examiner* — Joanne M Rodden
*Assistant Examiner* — Dana Stumpfoll
(74) *Attorney, Agent, or Firm* — Fish & Richardson P.C.

(57) ABSTRACT

An endoscopic vessel harvesting tool uses an optics system to present of a video image to a user. As the tool is manipulated around all sides of the vessel to dissect and cut surrounding tissue and side branches, the orientation of the captured image rotates. A motion tracker (e.g., gyrosensor) in the tool detects the rotation. By detecting a rotational angular velocity of the harvester handle during the harvesting procedure, the camera view orientation is compensated before display to the user. When the handle is rotated, the detected rotation is used to provide an opposite (canceling) rotation of the camera view so that a steady orientation is presented on the display. Thus, a vertically upward direction (or any other desired reference direction) remains substantially fixed in the displayed video images.

19 Claims, 8 Drawing Sheets

Related U.S. Application Data

(60) Provisional application No. 62/840,480, filed on Apr. 30, 2019.

(51) Int. Cl.

| | |
|---|---|
| *A61B 1/018* | (2006.01) |
| *A61B 17/00* | (2006.01) |
| *A61B 18/14* | (2006.01) |
| *A61B 1/04* | (2006.01) |
| *A61B 1/06* | (2006.01) |
| *A61B 18/00* | (2006.01) |
| *A61B 34/20* | (2016.01) |
| *A61B 90/00* | (2016.01) |
| *A61B 90/30* | (2016.01) |

(52) U.S. Cl.

CPC ............ *A61B 1/05* (2013.01); *A61B 18/1482* (2013.01); *A61B 1/018* (2013.01); *A61B 1/042* (2013.01); *A61B 1/0684* (2013.01); *A61B 2018/00404* (2013.01); *A61B 2034/2048* (2016.02); *A61B 2090/306* (2016.02); *A61B 90/37* (2016.02)

(58) Field of Classification Search

CPC .... A61B 2018/00404; A61B 2090/306; A61B 1/0684; A61B 1/042; A61B 1/05; A61B 10/04; A61B 17/32; A61B 1/018; A61B 1/012; A61B 1/055; A61B 1/06; A61B 10/02; A61B 10/0266; A61B 17/320016; A61B 17/32002; A61B 2017/320028; A61B 2017/320044; A61B 17/3205; A61B 2090/3614; A61B 2090/378; A61B 1/04; A61B 1/00066; A61B 1/00068; A61B 1/00119; A61B 1/00128

See application file for complete search history.

(56) References Cited

U.S. PATENT DOCUMENTS

| | | | |
|---|---|---|---|
| 7,547,314 | B2 | 6/2009 | Kadykowski |
| 8,465,488 | B2 | 6/2013 | Maeda et al. |
| 2005/0027167 | A1 | 2/2005 | Chatenever et al. |
| 2005/0080342 | A1* | 4/2005 | Gilreath ............. A61B 1/00087 128/903 |
| 2005/0119527 | A1* | 6/2005 | Banik ................ A61B 1/00066 600/117 |
| 2005/0272975 | A1* | 12/2005 | McWeeney ............ A61B 1/307 600/172 |
| 2008/0097471 | A1* | 4/2008 | Adams ............. A61B 17/12099 606/119 |
| 2008/0154091 | A1* | 6/2008 | Dejima .................. A61B 17/29 600/104 |
| 2008/0159653 | A1* | 7/2008 | Dunki-Jacobs ........ A61B 5/067 382/293 |
| 2010/0292533 | A1 | 11/2010 | Kasahara et al. |
| 2011/0230881 | A1 | 9/2011 | Maeda et al. |
| 2012/0289858 | A1 | 11/2012 | Ouyang et al. |
| 2013/0060249 | A1* | 3/2013 | Maeda ............... A61B 18/1482 606/42 |
| 2013/0281780 | A1 | 10/2013 | Kadykowski et al. |
| 2014/0285644 | A1 | 9/2014 | Richardson et al. |
| 2017/0027606 | A1* | 2/2017 | Cappelleri ............ A61B 1/018 |
| 2017/0042408 | A1 | 2/2017 | Washburn et al. |
| 2017/0265879 | A1 | 9/2017 | Washburn, II et al. |

FOREIGN PATENT DOCUMENTS

| | | |
|---|---|---|
| JP | 2008155030 A | 7/2008 |
| WO | WO 2012/151073 | 11/2012 |

OTHER PUBLICATIONS

Great Britain Search Report, Patents Act 1977: Search Under Section 18(3), Application No. GB2115168.3, dated Sep. 28, 2023.
Great Britain Search Report, Patents Act 1977: Search Under Section 17, Application No. GB2310991.1, dated Aug. 2, 2023.

* cited by examiner

ENDOSCOPIC VESSEL HARVESTER WITH GYROSENSOR ON HANDLE FOR ROTATING CAMERA VIEW

CROSS REFERENCE TO RELATED APPLICATIONS

This application is a continuation of PCT Application serial number PCT/US20/29498, filed Apr. 23, 2020, based on and claiming priority to U.S. Provisional Application Ser. No. 62/840,480, filed Apr. 30, 2019, both of which are incorporated herein by reference.

BACKGROUND OF THE INVENTION

The present invention relates in general to endoscopic harvesting of blood vessels or other tissues, and, more specifically, to presentation of a video image via an optics system in the endoscope to a user of the harvesting device.

In coronary artery bypass grafting (CABG), a blood vessel or vessel section, such as an artery or vein, is "harvested" (i.e., removed) from its natural location in a patient's body for use as a graft. After removal, the section of blood vessel is joined between an arterial blood source and the coronary artery that is to be bypassed. Among the preferred sources for the vessel to be used as the bypass graft are the saphenous vein in the legs and the radial artery in the arms.

A minimally-invasive technique employs a small incision for locating the desired vessel and for introducing one or more endoscopic harvesting devices. Primary dissection occurs by introduction of a dissecting instrument through the incision to create a working space and to partially separate the vessel from the surrounding tissue. Then a cutting instrument is introduced into the working space to sever the blood vessel from the connective tissue surrounding the section to be harvested and any side branches of the blood vessel. The branches may be clipped and/or cauterized.

In one typical procedure, the endoscopic entry site is located near the midpoint of the vessel being harvested, with dissection and cutting of branches proceeding in both directions along the vessel from the entry site. In order to remove the desired section of the blood vessel, a second small incision, or stab wound, is made at one end thereof and the blood vessel section is ligated. A third small incision is made at the other end of the blood vessel section which is then ligated, thereby allowing the desired vessel section to be completely removed through the first incision. Alternatively, only the first two incisions may be necessary if the length of the endoscopic device is sufficient to obtain the desired length of the blood vessel while working in only one direction along the vessel from the entry point.

An example of a commercially available product for performing the endoscopic vessel harvesting described above is the VirtuoSaph™ Endoscopic Vein Harvesting System from Terumo Cardiovascular Systems Corporation of Ann Arbor, Michigan. Endoscopic vessel harvesting systems are described in U.S. Pat. No. 8,465,488 to Maeda et al and U.S. Pat. No. 7,547,314 to Kadykowski, both of which are incorporated herein by reference in their entirety. In the VirtuoSaph™ System, the cutting tool for severing and cauterizing branches has the form of a V-cutter wherein a V-shaped tip is extendable from the distal end of the unit to guide a branch to be cut into a longitudinal slit. Electrodes adjacent the slit are electrically energized with a high frequency voltage in order to cauterize and sever the branch by coagulation. A V-keeper also extends from the distal end in order to capture the vessel and guide the tool along the vessel.

An internal endoscopic view is provided to the user via an optical system having a camera and a video display. The camera can be mounted within the distal tip of the harvesting device. Alternatively, a lens and optical fiber installed in the harvesting device can carry an image to a camera located at a remote end of the optical fiber outside the harvesting device or in the handle of the device. In any case, an image has been obtained using fixed optics in the distal tip, resulting in rotation of the image presented on the display when the harvesting device is rotated about its longitudinal axis as it is manipulated by the user. For example, the V-cutter and V-keeper may remain oriented at the right and left sides of the video image regardless of any rotational movement of the tool as it is moved along and around the vessel. Consequently, the relatively stationary elements in the image such as the vessel, the branches, and the connective tissue appear to rotate in an opposite direction from the rotation of the tool. The image rotation may be counterintuitive and requires additional skill for the user to properly interpret the images.

In the VirtuoSaph™ System, it is possible to hold the camera head located at the handle of the harvester device to prevent it from rotating with the handle in order to prevent the image rotation. However, the process is time consuming, and it would be desirable the relieve the user from the need of separately manipulating the camera head to maintain a desired image orientation.

SUMMARY OF THE INVENTION

The invention corrects the camera view orientation by detecting a rotational angular velocity of the harvester handle during the harvesting procedure. When the handle is rotated, the detected rotation is used to provide an opposite (canceling) rotation of the camera view so that a steady orientation is presented on the display. Thus, a vertically upward direction (or any other desired reference direction) remains substantially fixed in the displayed video images.

In one aspect of the invention, an endoscopic harvesting system comprises a harvesting device for insertion into a patient and having a handle. An optical system provides an image showing a field of view at a distal end of the harvesting device opposite from the handle. An angular motion sensor is mounted for rotation with the optical system and provides a rotation signal in response to angular rotation around a longitudinal axis of the harvesting device. An image processor receives the image from the optical system and receiving the rotation signal, wherein the image processor generates a video output signal which is compensated by applying a counter-rotation to the image in response to the rotation signal.

DETAILED DESCRIPTION OF PREFERRED EMBODIMENTS

Figures 1, 3:
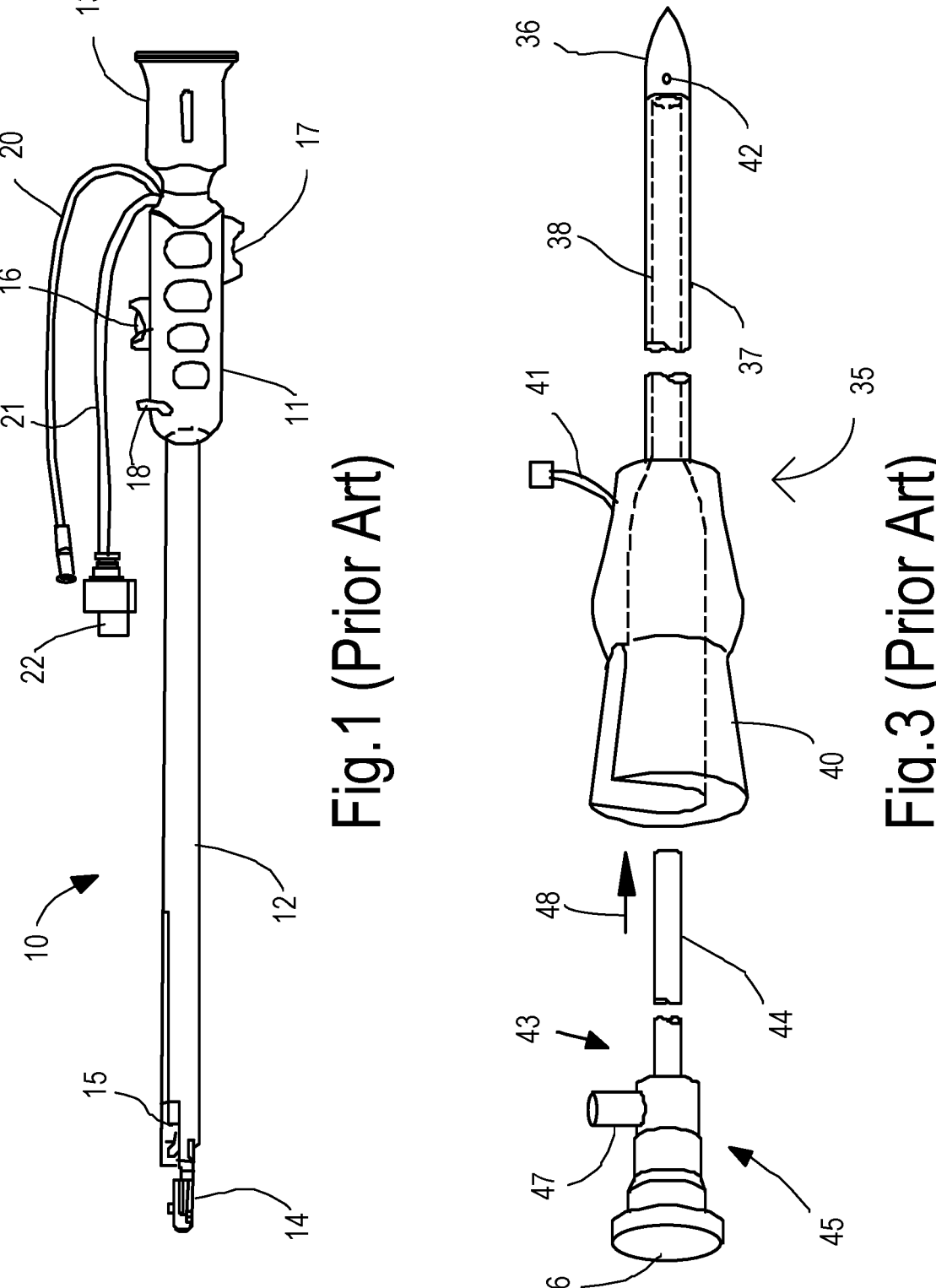
FIG. 1 is a side view of a conventional harvester unit.
FIG. 3 is a side view of a conventional dissector unit and an endoscope unit.

FIG. 1 shows a harvester rod 10 used to grasp the target vessel being dissected and to sever any branches or connective tissue connecting to the vessel. Harvester rod 10 is inserted into a working tunnel along a target vessel that is created using a dissector rod (see, e.g., FIG. 4). Harvester rod 10 has a handle 11 connected to an elongated sleeve member or insertion member 12 and to an endoscope receiver 13. At the distal end of insertion member 12 are a vessel-keeper (V-keeper) 14 which is a capture frame for retaining the vessel being dissected and a V-cutter 15 for severing side branches and connective tissue. V-keeper 14 is manipulated by V-keeper buttons 16 on handle 11. V-cutter 15 is extended or retracted by manipulating a V-cutter extender button 17 on handle 11. An insufflator tube 20 can be connected to a source of gas such as $CO_2$ to deliver insufflation gas to the distal end of insertion member 12. A bipolar cord 21 has a connector 22 at one end for connecting to a source of high frequency voltage, and includes conductors for supplying the voltage to electrodes on V-cutter 15.

Figure 2:
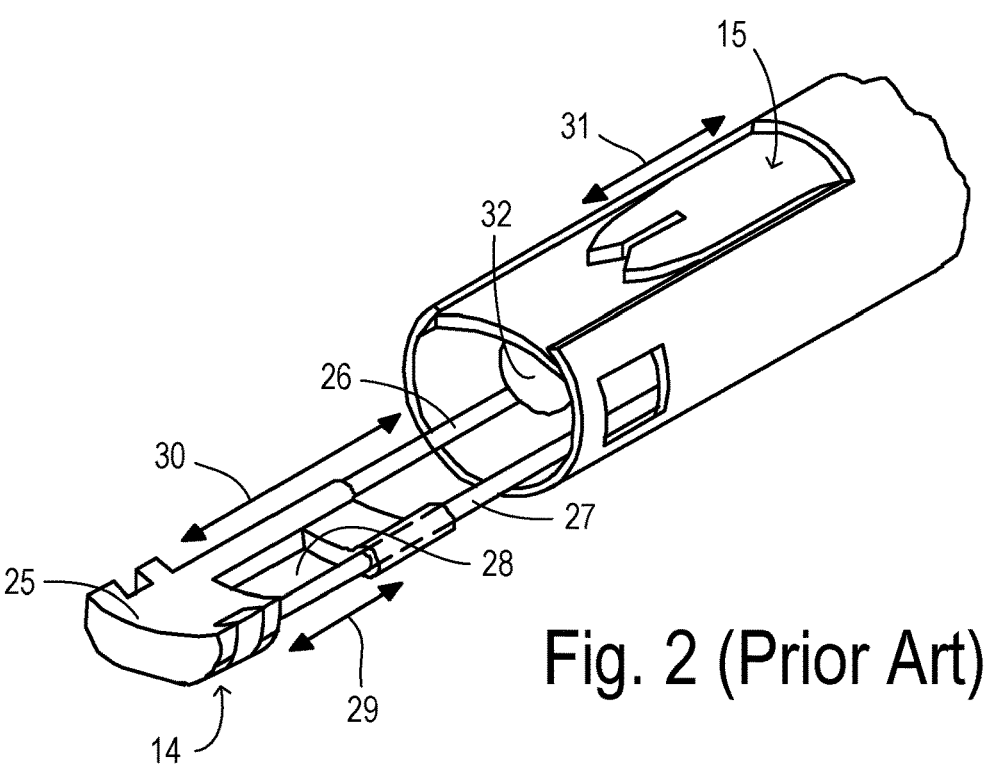
FIG. 2 is a perspective view showing a V-keeper and a V-cutter of FIG. 1 in greater detail.

V-keeper 14 and V-cutter 15 are shown in greater detail in FIG. 2. V-keeper 14 includes a guide frame 25 mounted to a support rod 26 and a movable rod 27. Guide frame 25 and rod 27 together form the capture frame with an internal opening 28. The vein or other vessel to be harvested is maneuvered into opening 28, and then the V-keeper buttons on the handle are manipulated to extend rod 27 along one side of the capture frame in order to close opening 28 and thereby retain the vessel. V-cutter 15 includes a V-tip with a central slit mounted to an extendable guide that is manipulated by the V-cutter button on the handle in order to place side branches into the slit.

V-keeper 14 is longitudinally extendable as shown by arrow 30 while rod 27 is independently longitudinally extendable as shown by arrow 29. In FIG. 2, rod 27 is in an extended position used for maintaining the vessel being harvested within opening 28 (i.e., the side of the capture frame is closed).

V-cutter 15 is longitudinally extendable in the directions shown by arrow 31. Elongated insertion member 12 has a notch with a terminal edge which exposes V-cutter 15 prior to being extended further than the end of insertion member 12. A lens portion 32 at the end of the endoscope is shown positioned near the distal end of member 12. Lens portion 32 may be a lens integrated with a camera (i.e., image sensor) or placed at the end of an optical fiber which is connected to a camera at its other end.

The working tunnel into which member 12 is inserted can be created using a blunt dissector device 35 shown in FIG. 3, which likewise receives a rigid endoscope 43 (or could alternatively include a camera affixed within a transparent tip 36). Endoscope 43 has a rigid endoscope rod 44 extending to a distal end and being connected to an endoscope head 45 at its proximal end. Head 45 includes an eyepiece 46 and a light connector 47. Eyepiece 46 can be viewed directly or can be coupled to a camera for presenting a video image on a display. Dissector 35 includes a dissector rod having an outer sheath 37 with an internal bore 38. Sheath 37 is connected to blunt dissector tip 36 at the distal end. A handle 40 at the proximal end of dissector 35 axially receives endoscope 43 (in the direction shown by arrow 48) so that endoscope rod 44 is inserted into bore 38 until it enters hollow tip 36 to allow visualization by the endoscope of an area being dissected through transparent tip 36. A space within bore 38 not occupied by endoscope rod 44 and/or additional passages within sheath 37 couple a gas inlet tube 41 at handle 40 with a gas outlet hole 42 at the distal end in either sheath 37 or tip 42 for the purpose of introducing insufflation gas to inflate a subcutaneous space around the dissection site.

Figure 4:
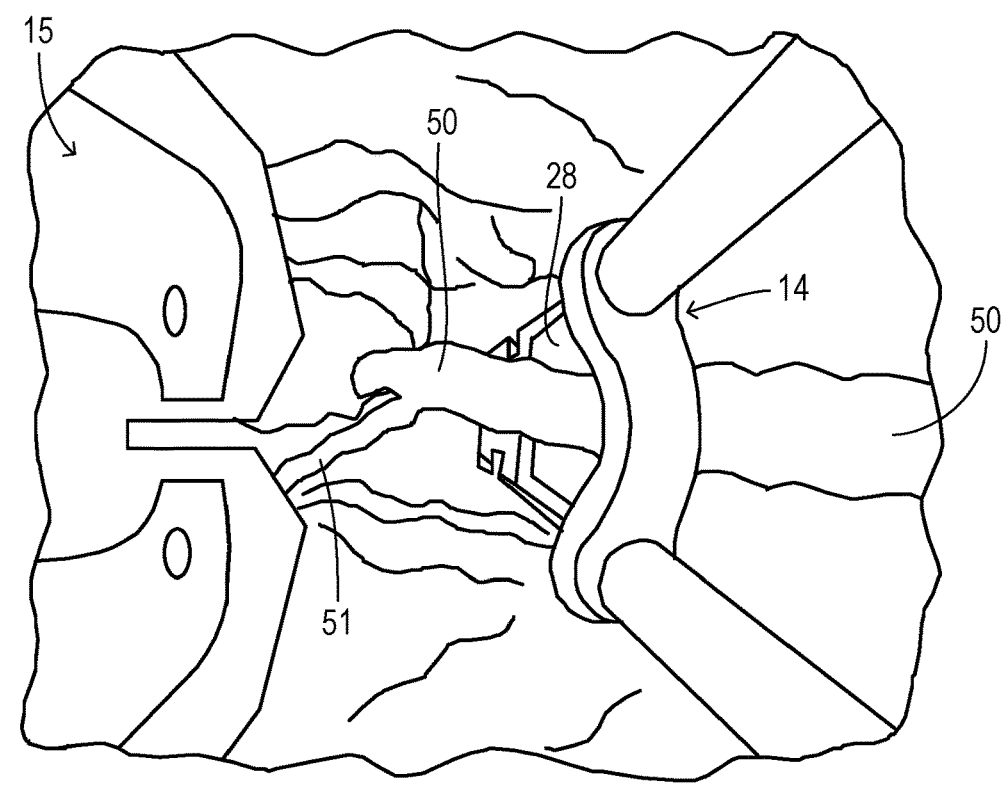
FIG. 4 is a camera view depicting the V-keeper and V-cutter of the harvester unit deployed within a working tunnel around a target vessel.

FIG. 4 is an endoscopic view as seen during vessel harvesting wherein a target vessel (e.g., saphenous vein) 50 is retained within opening 28 of V-keeper 14 within a cavity around vessel 50 created previously during blunt dissection. V-cutter 15 is in position for extending toward a side branch 51 for cauterizing and severing it to prepare a section of vessel 50 for removal. Since side branches such as side branch 51 extend in various radial directions away from vessel 50, the harvester must be rotated around vessel 50 to directly approach all the different side branches. If lens portion 43 is allowed to rotate around the longitudinal axis of member 12 during manipulations by the user, then the resulting video image from the endoscope rotates in an opposite direction. The orientation of V-keeper 14 and V-cutter 15 stays fixed on the video display regardless of how much they are rotated with respect to the patient. During the procedure, the target vessel and the view direction along the tunnel extend generally horizontally. However, the upward direction (e.g., with respect to the patient and with respect to the room within which the user is standing) which extends transversely from vessel 50 in the video image shifts around the image as the harvester rotates. It would be desirable to provide a stable image of the patient anatomy so that the real upward direction (or any other chosen reference) stays at the top of the video images (i.e., so that the image does not rotate with respect to the patient's anatomy).

Figures 5, 6, 7:
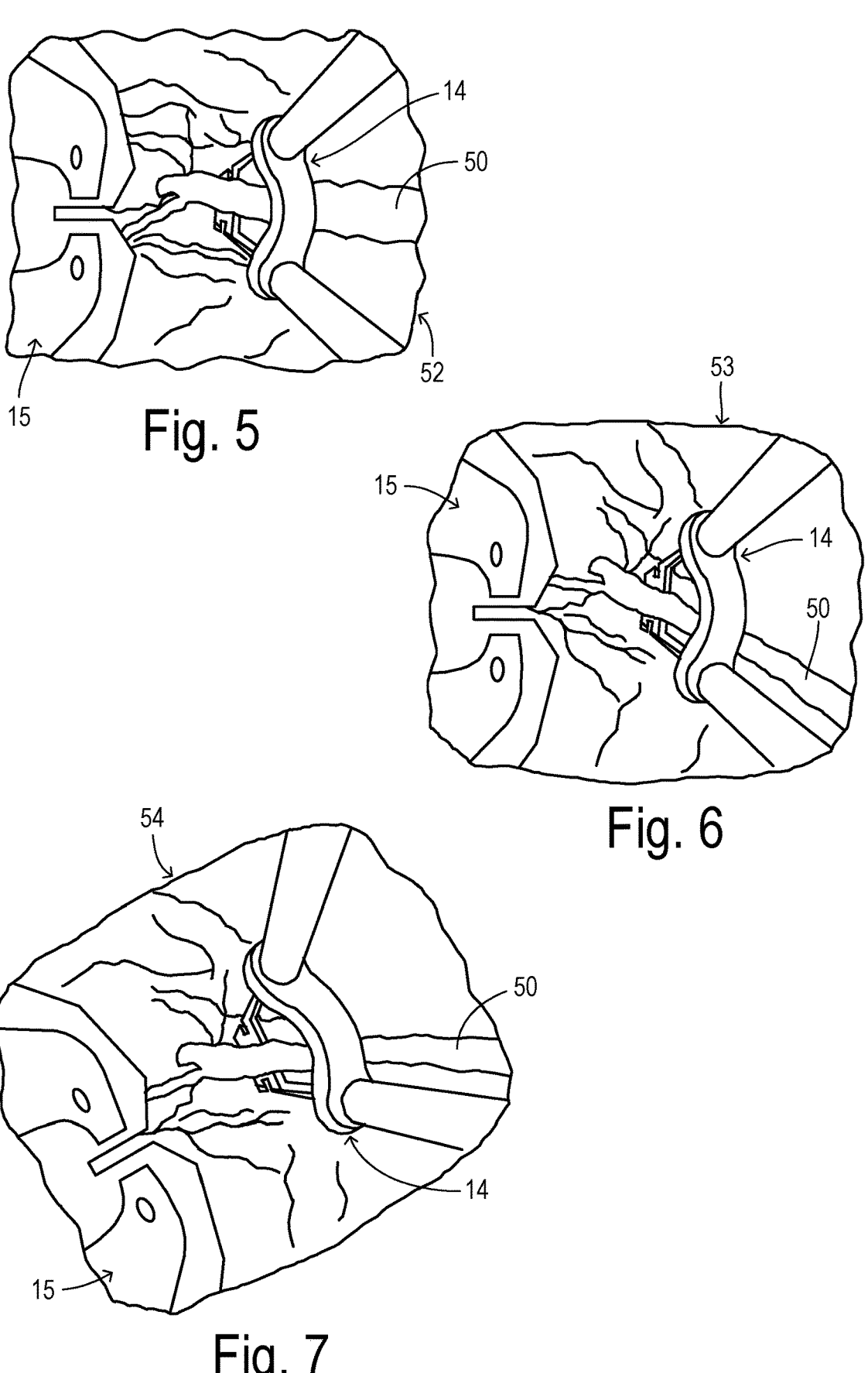
FIGS. 5 and 6 are camera views before and after a counterclockwise rotation of the harvester unit without the image compensation of the invention.
FIG. 7 is a camera view after applying image compensation to the camera view of FIG. 6.

FIG. 5 shows an initial video image 52 during a procedure resulting with the harvester unit and the camera image aligned to a first rotational position. V-cutter 15 and V-keeper 14 are oriented at the left and right sides, respectively, of image 52, and vessel 50 extends in a 3 o'clock direction. By rotating the harvester unit and camera image slightly in a counterclockwise direction, the image captured by the camera rotates in a clockwise direction, so that vessel 50 extends in a 4 o'clock direction as shown in FIG. 6. It would be beneficial for a user to present video images that reflect the rotational movement of the harvester unit, as shown in FIG. 7 wherein V-cutter 15 and V-keeper 14 have rotated counterclockwise and vessel 50 continues to extend in a 3 o'clock direction.

In the present invention, the optical system utilizes a camera to obtain a video image to be electronically processed and shown to the user on a video display. The camera may be placed either at an eyepiece at the end of a rigid endoscope rod or at a distal tip or end of a harvesting device that is inserted into a patient. The camera or other parts of the optical system are allowed to rotate along with the harvesting device, causing the camera image to rotate accordingly. However, the device rotation is measured and then used to apply a counter-rotation to the image being sent to the display so that the video image seen by the user maintains a fixed orientation with respect to the patient. The device rotation may be measured using a motion tracker, gyroscope, accelerometer, or other device which is mounted to the camera unit, harvester unit, dissector unit, or other structure that rotates along with the camera.

Figure 8:
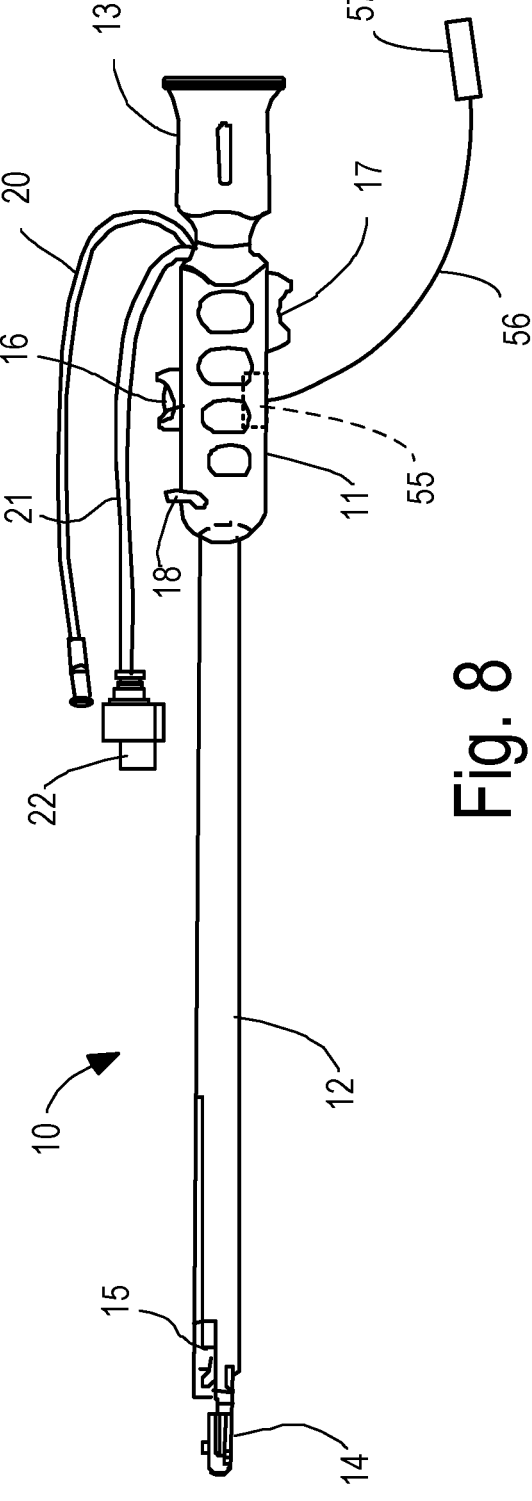
FIG. 8 is a side view of a harvester unit having a motion tracking sensor of the present invention.

Referring to FIG. 8, a first example is shown wherein a motion tracker device 55 in mounted within handle 11 of harvester unit 10. For example, motion tracker 55 may be comprised of an integrated circuit assembly such as the HiLetgo MPU9250/6500 9-Axis 9-DOF 16-Bit Gyroscope Acceleration Magnetic Sensor available from Shenzhen HiLetgo Technology Co., Ltd., of Shenzhen, Guangdong, China. A cable 56 and connector 57 carry power input from and sensor output signals (e.g., an angular velocity signal) to a processor or module for handling video signals and driving a display monitor (not shown).

Figure 9:
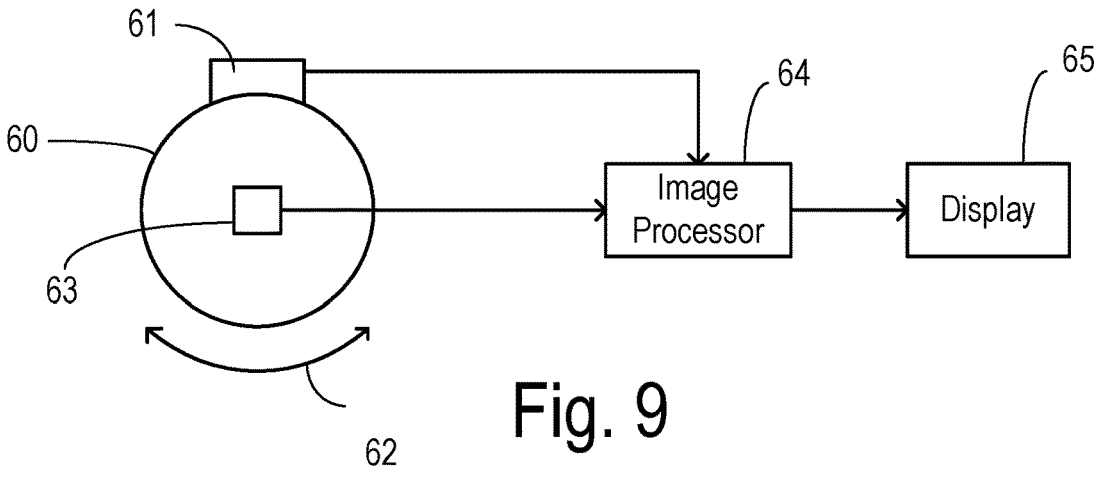
FIG. 9 is a block diagram showing a first embodiment of the invention.

More particularly, FIG. 9 shows an embodiment wherein a structural portion 60 of a harvesting system (e.g., a camera unit, a handle or rod portion of a harvester unit or a dissector unit) carries a gyrosensor 61 which generates an angular rate (i.e., angular velocity) signal according to an axial rotation 62 of structural portion 60. In one example, a piezoelectric gyrosensor can be used. Alternatively, other types of motion sensors, accelerometers, or vibration sensors can be used. A camera 63 captures an endoscopic view encoded in electrical signals provided to an image processor 64. Image processor 64 receives the angular rate signal, which it uses to apply a corresponding counter-rotation to the endoscopic view presented to a display panel 65.

Figure 10:
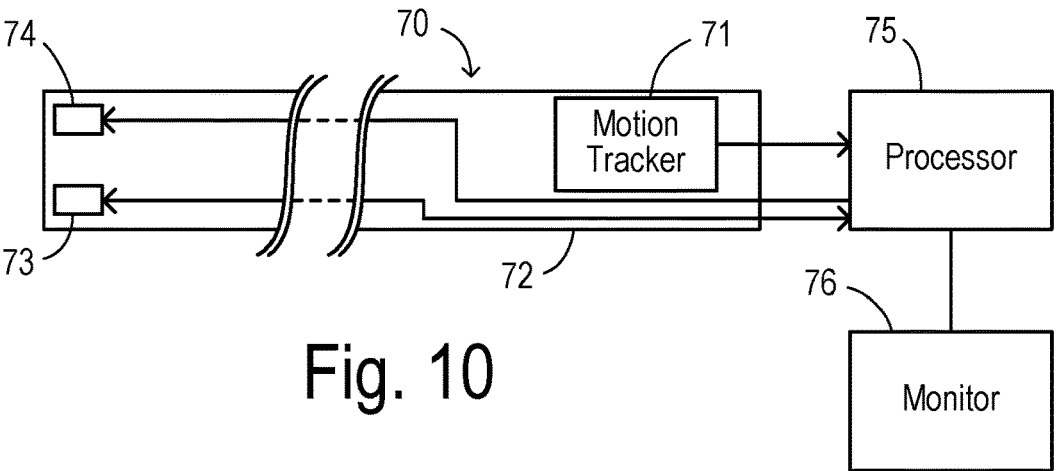
FIG. 10 is a block diagram showing a second embodiment of the invention.

FIG. 10 shows another embodiment wherein a camera unit 70 (for insertion into a harvester or dissector unit) incorporates a motion tracker 71. Motion tracker 71 may include a multi-chip module which is sufficiently small to easily fit within camera unit 70, preferably near its proximal end. Camera unit 70 has an extended body 72 including a distal end carrying a camera sensor 73 and an LED illumination source 74. Motion tracker 71, camera 73, and LED 74 are electrically coupled to a processor 75 for providing power to LED 74 and receiving video frames from camera 73, for example. Processor 75 may be comprised of a microcomputer (e.g., a PC) or a custom electronics module. Processor 75 provides power to motion tracker 74 in order to operate a gyroscope, accelerometer, or other sensing components of motion tracker 71 in order to generate angular velocity signals provided to processor 75. Using the angular velocity signals, processor 75 detects rotation of camera unit 70 and applies a counter rotation to video frames received from camera 73 before forwarding the video frames for display on a monitor 76. As known in the art, motion tracker 71 may include a three-axis accelerometer and three-axis gyroscope which sends various motion signals tracking the motion of the sensor unit. The motion signals may be used to calculate a Euler angle or a Quaternion using known methods to detect the device position (e.g., as commonly used with handheld gaming controllers). With the resulting device positions and change in position per unit time based on the angular velocity signals, processor 75 determines a current orientation of the camera view (e.g., an rotation angle of the current position from a default position) and determines a correct view angle for slewing the video image in order to keep a desired orientation.

A personal computer (PC) or other computing device may be used which integrates processor 75 and monitor 76. Alternatively, a separate monitor can be used which receives and HDMI or RCA video signal from processor 75. A graphical user interface (GUI) may be provided by the computing device or custom module to present various added functions to the user. For example, a GUI may display a calculated orientation angle of the tool and other camera information such as pixel resolution, frame rate, and magnification (which can be made adjustable). The GUI may include a box for setting an offset angle and a button for initiating the capturing of images (e.g., still images or video).

Figure 11:
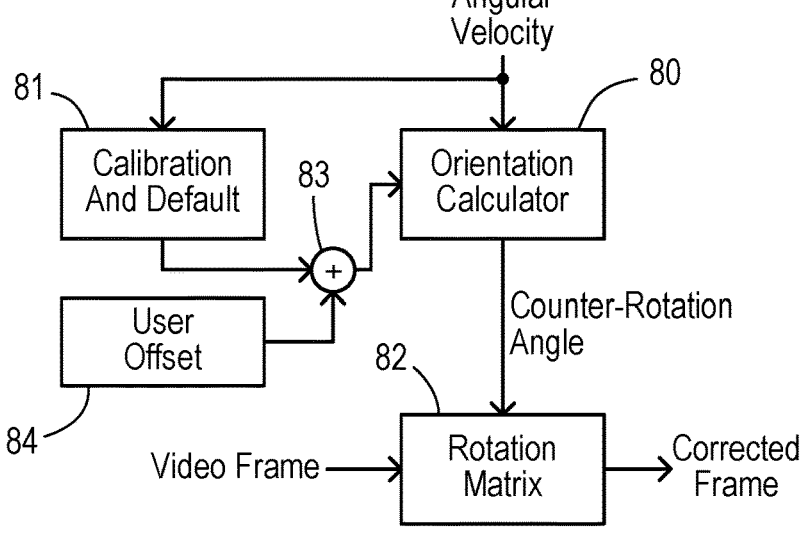
FIG. 11 is a block diagram showing image compensation according to one embodiment of the invention.

FIG. 11 shows a block diagram depicting one example of processor functions for accomplishing the desired image rotation. The angular velocity signal is provided to an orientation calculator block 80 and to a calibration and default block 81. Block 81 provides a desired reference orientation to orientation calculator 80. Based on a difference between the desired reference and the actual instantaneous orientation, a counter-rotation angle is provided from block 80 to a rotation matrix block 82. Video frames fed to rotation matrix block 82 are rotated according to the counter-rotation angle, and corrected video frames are output from rotation matrix block 82 to a video monitor.

Calibration/default block 81 may store a preferred spatial orientation setting for the top of the displayed image, such as vertically upward (i.e., pointing in an azimuth direction opposite to the pull of gravity). The preferred orientation setting may be obtained as a result of a calibration procedure performed by block 81 in which the harvester unit or dissector unit containing the camera unit is placed motionless in a horizontal position (or other arbitrary orientation) and motion tracker signals are obtained which identify the vertical axis (and which may be compared with sensor signals at later times to determine a difference between a subsequent position and the default orientation). The default orientation may be provided to one input of a summer 83 which provides its output to an input of orientation calculator 80. A second input of summer 83 may receive a user offset value from a user offset block 84 which permits a user to specify a different preferred camera view (so that a different direction may appear at the top of the video monitor, if desired). When the user offset value is zero, then the default orientation is used unmodified. User offset block 64 may include an input device or keypad for manually inputting a desired offset, for example.

Figure 12:
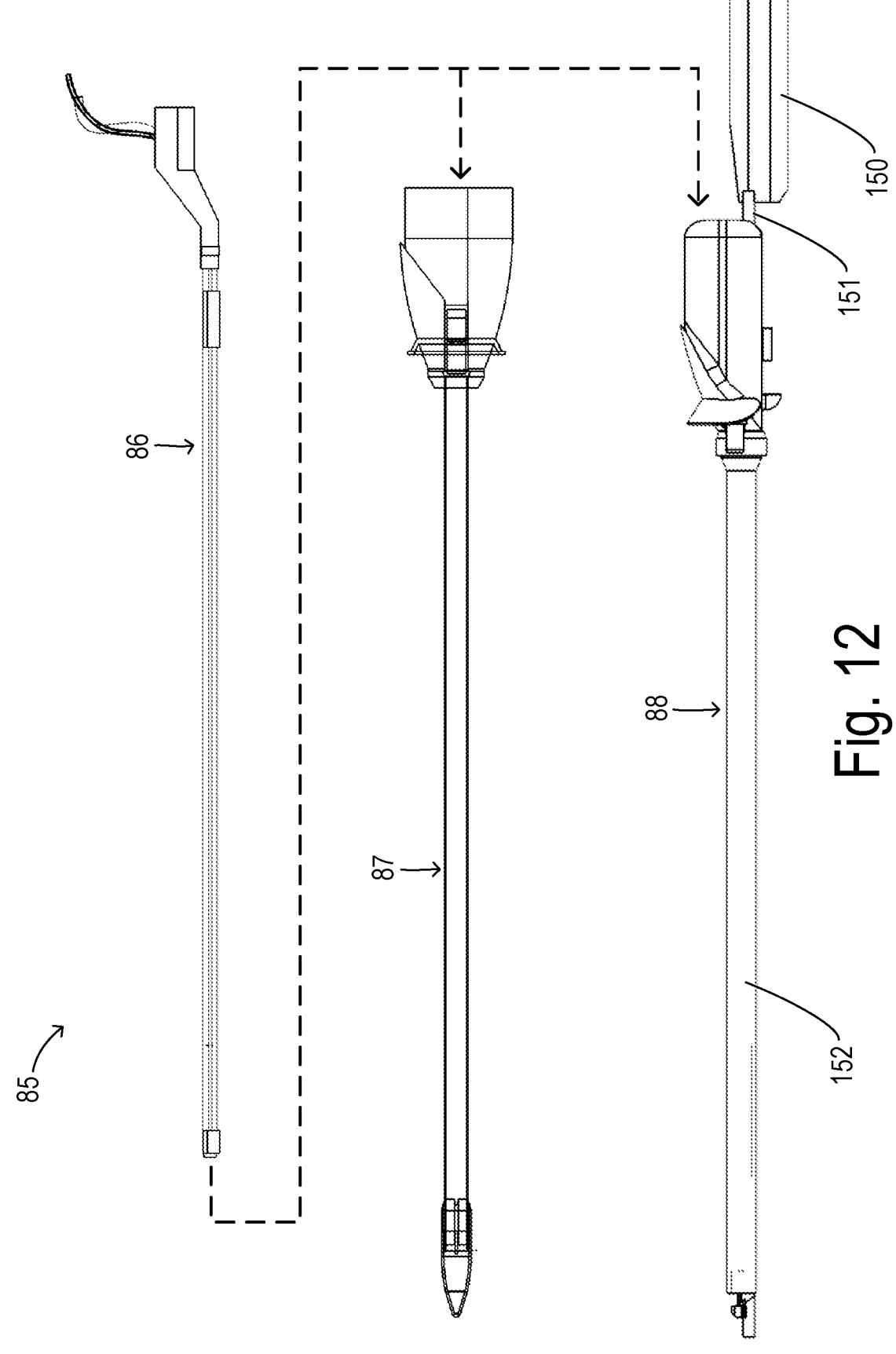
FIG. 12 is a side view of the components of a vessel harvesting system according to another embodiment.
Figures 13, 14:
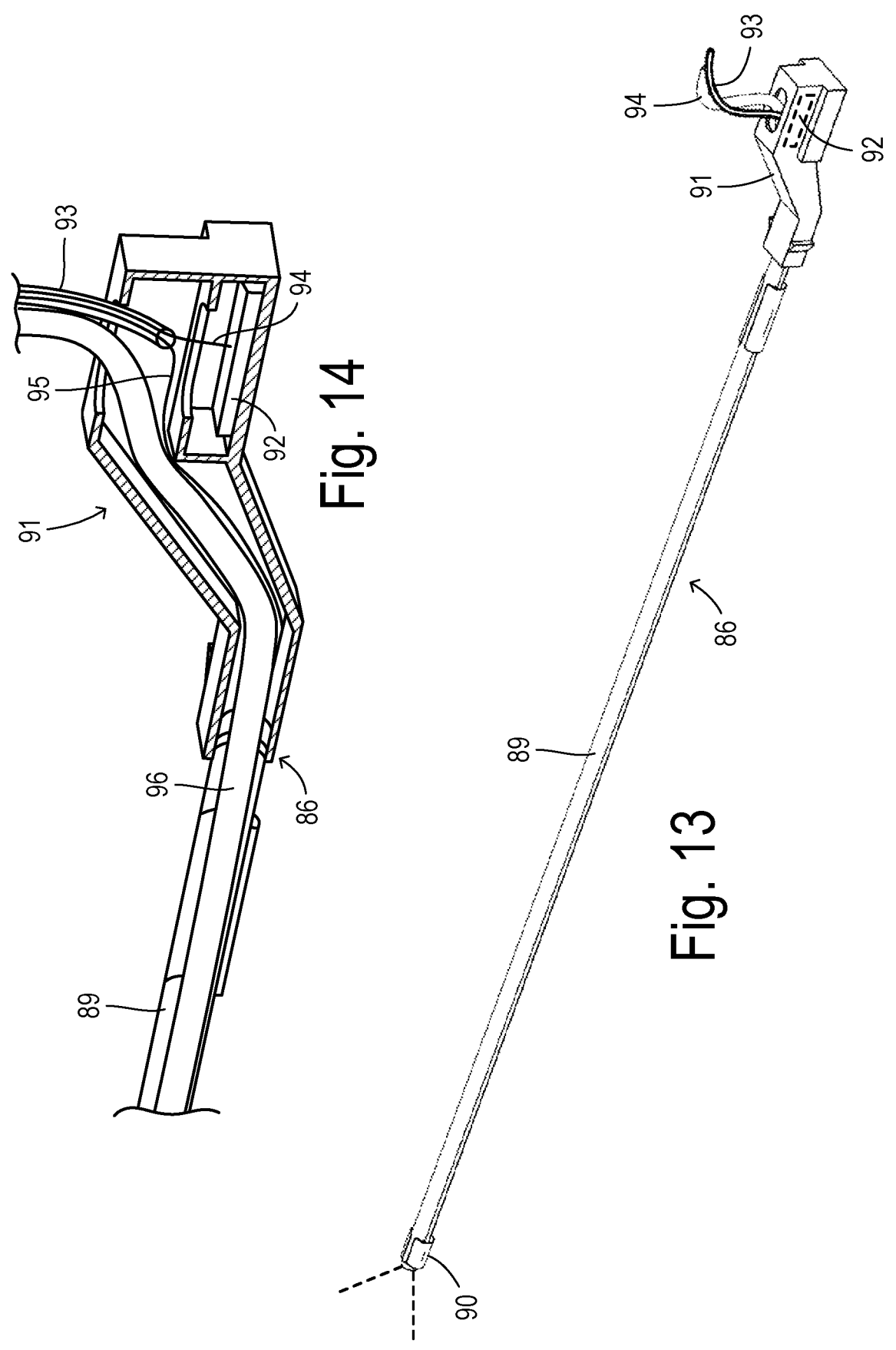
FIG. 13 is a perspective view showing the camera unit of FIG. 12 in greater detail.
FIG. 14 is a cross-sectional, perspective view depicting a motion tracking sensor in the camera unit of FIG. 12.

FIG. 12 shows a harvester system 85 including a camera unit 86, a dissector unit 87, and a harvester (cutting) unit 88. Dissector unit 87 and harvester unit 88 have central passages adapted to receive camera unit 86. As shown in FIGS. 13 and 14, camera unit 86 has a distal end 90 and a proximal end 91. A lens and/or camera and a light source (e.g., an LED or the outlet end of a light pipe fed at its other end by a remote light source) are mounted at distal end 90 to provide an endoscopic view when camera unit 86 is installed in dissector unit 87 or harvester unit 88. A lengthwise conduit 89 between proximal end 91 and distal end 90 conveys electrical cables 95 for the camera/LED as well as insufflation tubing 96 for providing a flow of the insufflation gas to distal end 90, where openings communicate the insufflation gas into the working tunnel.

At proximal end 91 of camera unit 86, a motion tracking sensor device 92 is mounted in a recess 94. A wire bundle 93 carries an electrical cable 94 for sensor device 92 and cable 95 for the camera/LED devices out from camera unit 86 to extend to the processor via an electrical connector at the end of bundle 93 (not shown). A connector at the end of tubing 96 connects to a source of $CO_2$ insufflation gas. By integrating the insufflation gas delivery into camera unit 86 (instead of having the insufflation tubing carried by the dissector and harvester units), the steps to switch between using the dissector and the harvester are simplified since there is no need to switch out the $CO_2$ tubing. In prior art harvesting devices (e.g., for blood vessels or other internal tissues), a probe for coupling the electrical energy and other accessories (such as cutting jaws) for performing other functions are rotated (e.g., around the endoscope), including a light cable which has been connected perpendicularly to the longitudinal direction of the device. Consequently, the probe or accessories are prone to hit the light cable when they are rotated. To improve usability, the invention enables a camera cable to be integrated with other cables.

One important advantage of the embodiment shown in FIG. 12 relates to the center of rotation when the device is maneuvered inside the body. Harvester unit 88 includes an insertable jaw/cutter element with a handle 150 and a longitudinal body 151 extending to the jaws, wherein longitudinal body 151 has a center longitudinal axis slightly offset from a center longitudinal axis of a main outer sheath 152. In many conventional devices, the center of rotation coincides with the axis of the endoscope unit/camera head (due to the weight of the endoscope and because the user is grasping the camera head in one hand to keep the camera and the view orientation from rotating). In such a case, the view of the cutter (e.g., V-cutter or jaws) and of a spacer (e.g., C-ring), V-keeper, or other tools at the distal end will revolve around the axis of the endoscope, which makes guiding and using the tools more difficult for the user. In order to put the device into a position for making a cut, for example, the user must 1) maneuver the device forward and back, 2) rotate the device according to the endoscope axis, and 3) revolve both the jaws and the spacer together. By offsetting the longitudinal axis of body 151, the view orientation from camera unit 86 can be configured to rotate about the jaws/cutter. In order to put the device if FIG. 12 into a position for making a cut or grasping in the jaws, the user only needs to maneuver the device forward and back and then rotate as needed (i.e., without needing to revolve the jaws).

Figure 15:
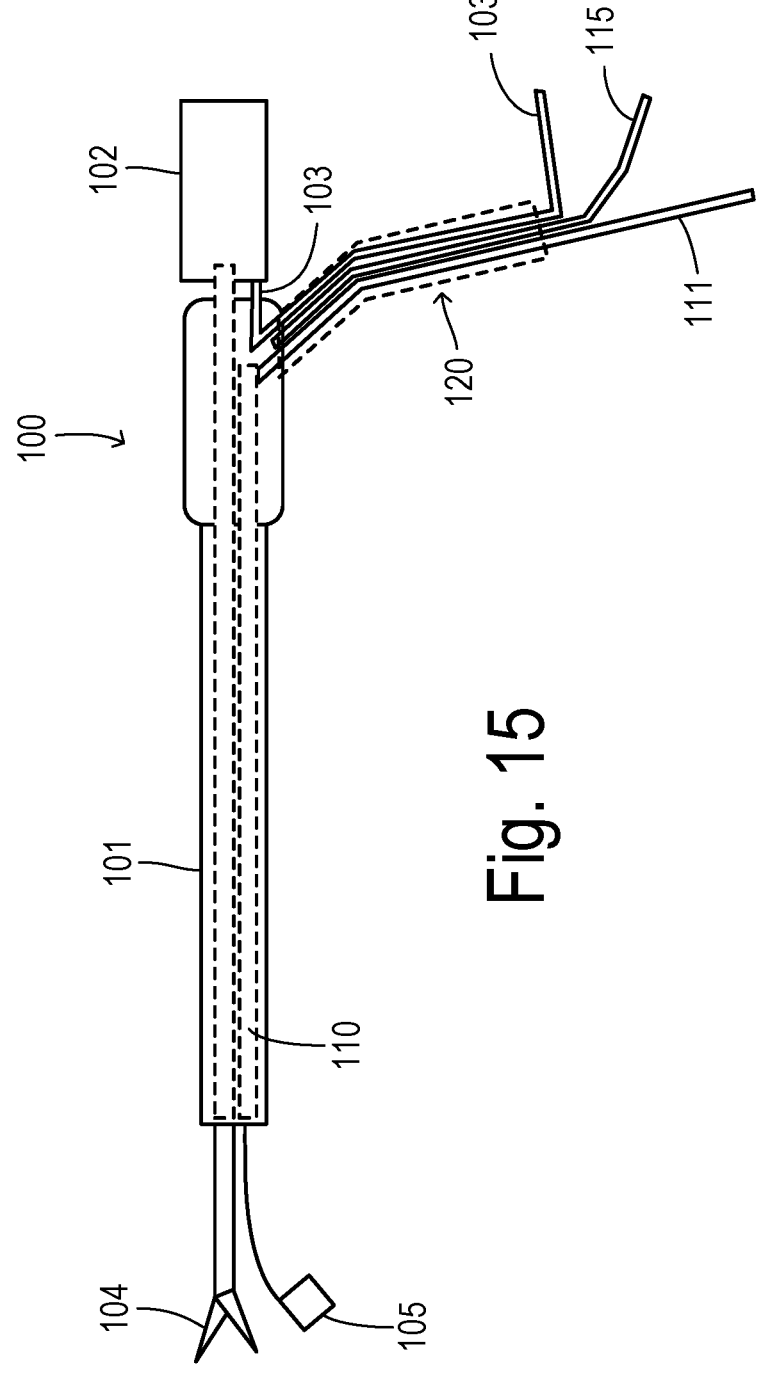
FIG. 15 is a side view of a harvesting unit according to another embodiment of the invention.

FIG. 15 shows another improved harvester device 100 wherein fixed optics are contained within the device and the gyrosensor is used to compensate a display video signal to eliminate rotations of the image. As a result of the optics being self-contained within the harvester device, the integrated cables are easily managed and interference with an energy probe is avoided. A longitudinal rod 101 is configured to retain a cutting unit having a proximal head unit 102 and a distal jaw unit 104. A power cable 103 supplies power through head unit 102 to bipolar cutting electrodes (not shown) in jaw unit 104. Head unit 102 may include control mechanisms for manipulating jaw unit 104 and a spacer (e.g., C-ring) tool 105 which guides a vessel.

A fixed camera unit 110 has a camera, light source, and gyrosensor sharing an associated electrical cable 111. Insufflation tubing 115 extends from the distal end of rod 101 out through the proximal end. A bundle (e.g., jacket or wrap) 120 ties together cable 103, cable 115, and tubing 115, providing an uncluttered, easy to use harvesting tool.

In addition to the integrated cables/tubing of FIG. 15, this embodiment may also be easily configured to provide a handle of head unit 102 and/or a main device handle with a longitudinal axis coincident with distal jaw unit 104 (i.e., offset from the camera axis).

The device shown in FIG. 15 can be configured as either a harvester device for cutting/cauterizing tissue or as a dissector device for blunt dissection of a tunnel around a target vessel. In addition, the device could be configured to incorporate the functions of both a dissector and a harvester device (i.e., a procedure for harvesting a vessel could be completed without the need of a separate dissector). A procedure using the combined configuration can be completed more quickly and easily since the switching out of separate devices is avoided.

What is claimed is:

1. An endoscopic harvesting system, comprising:
   a harvesting device for insertion into a patient, the harvesting device comprising a longitudinal axis, a body, and a handle, the body comprising a distal end, a proximal end, and a bore extending between the proximal end and distal end of the body, wherein the handle is coupled to the proximal end of the body;
   an optical system providing an image showing a field of view at the distal end of the harvesting device opposite from the handle, the optical system comprising a camera unit insertable into the bore of the harvesting device, wherein the camera unit comprises a proximal end, a distal end, a conduit extending between the proximal end and the distal end, and a housing coupled to the conduit at the proximal end;
   an angular motion sensor mounted within the housing of the camera unit for rotation with the optical system and providing a rotation signal in response to angular rotation around the longitudinal axis of the harvesting device;
   an image processor receiving the image from the optical system and receiving the rotation signal, wherein the image processor generates a video output signal which is compensated by applying a counter-rotation to the image in response to the rotation signal; and
   an insufflation tube extending longitudinally in the conduit of the camera unit and extending through the housing and out from the proximal end of the camera unit,
   wherein the housing comprises a distal end defining a distal opening and a proximal end defining a proximal opening, wherein the distal end is coupled to the conduit, and wherein the angular motion sensor is mounted at the proximal end of the housing, and
   wherein, relative to a transverse axis of the longitudinal axis of the harvesting device, the angular motion sensor is mounted (i) below the proximal opening through which the insufflation tube extends out from the camera unit, and (ii) above the distal opening.

2. The endoscopic harvesting system of claim 1, wherein the angular motion sensor is comprised of a gyrosensor.

3. The endoscopic harvesting system of claim 1, wherein the angular motion sensor is comprised of an accelerometer.

4. The endoscopic harvesting system of claim 1, wherein the angular motion sensor is comprised of a multi-axis motion tracker.

5. The endoscopic harvesting system of claim 1, wherein the image processor is configured to calculate a current orientation according to the rotation signal, determine a difference between the current orientation and a reference orientation, and counter-rotate video frames of the video output signal according to the difference.

6. The endoscopic harvesting system of claim 5 wherein the image processor is configured to calibrate to a default rotational orientation.

7. The endoscopic harvesting system of claim 6 wherein the image processor is configured to counter-rotate the video frames to maintain the default rotational orientation in a visual display of the video frames.

8. The endoscopic harvesting system of claim 6 further comprising a user input for providing a user offset, wherein the image processor is configured to counter-rotate the video frames to maintain an offset rotational orientation in a visual display of the video frames.

9. The endoscopic harvesting system of claim 1, wherein the optical system comprises an image sensor mounted at the distal end of the camera unit.

10. The endoscopic harvesting system of claim 9 wherein the optical system further comprises a light source at the distal end of the camera unit.

11. The endoscopic harvesting system of claim 10, comprising:

cables connected to the angular motion sensor, the image sensor, and the light source and extending out from the proximal end of the camera unit;

wherein the cables and the insufflation tube are bundled at the proximal end of the harvesting device.

12. The endoscopic harvesting system of claim 1, wherein the camera unit comprises:

an optical fiber extending longitudinally through the camera unit;

a lens mounted at a distal end of the optical fiber; and an image sensor disposed at a proximal end of the optical fiber.

13. The endoscopic harvesting system of claim 1 wherein the harvesting device comprises a dissector unit, wherein the dissector unit comprises a bore sized to receive the camera unit.

14. The endoscopic harvesting system of claim 1 wherein the harvesting device comprises a cutting unit insertable into the bore of the harvesting device, the cutting unit comprising a proximal end, a distal end, a handle at the proximal end, a cutter assembly at the distal end, and a body extending longitudinally between the handle and the cutter assembly.

15. The endoscopic harvesting system of claim 1 wherein the harvesting device comprises a combination dissector and cutting unit.

16. The endoscopic harvesting system of claim 1 wherein:

the harvesting device has a center rotational axis when inserted into the patient;

the optical system has a center axis within the field of view in the image; and the center rotational axis of the harvesting device is offset from the center axis of the optical system such that the field of view of the image is rotatable about the center rotational axis of the harvesting device when the camera unit is inserted into the harvesting device.

17. The endoscopic harvesting system of claim 14, wherein when the body of the cutting unit is inserted into the bore of the body of the harvesting device, a longitudinal axis of the cutting unit is offset from the longitudinal axis of the harvesting device.

18. The endoscopic harvesting system of claim 17, wherein when the camera unit and the cutting unit are inserted into the bore of the body of the harvesting device, a center rotational axis of the harvesting device is offset from a longitudinal axis of the optical system such that the field of view of the image is rotatable about the center rotational axis of the harvesting device.

19. The endoscopic harvesting system of claim 17, wherein the cutter assembly is configured to cut a vessel and/or grip a vessel and/or guide a vessel of the patient.

* * * * *